(12) United States Patent
O'Donnell et al.

(10) Patent No.: US 6,892,926 B2
(45) Date of Patent: May 17, 2005

(54) TOUGHNESS-OPTIMIZED WELD JOINTS AND METHODS FOR PRODUCING SAID WELD JOINTS

(75) Inventors: Jeffrey R. O'Donnell, Sugar Land, TX (US); Ronald R. Bowen, Magnolia, TX (US)

(73) Assignee: ExxonMobil Upstream Research Company, Houston, TX (US)

( * ) Notice: Subject to any disclaimer, the term of this patent is extended or adjusted under 35 U.S.C. 154(b) by 66 days.

(21) Appl. No.: 10/633,134

(22) Filed: Aug. 1, 2003

(65) Prior Publication Data

US 2004/0069831 A1 Apr. 15, 2004

Related U.S. Application Data

(60) Provisional application No. 60/417,974, filed on Oct. 11, 2002.

(51) Int. Cl.[7] ............................................. B23K 31/00
(52) U.S. Cl. ............................. 228/104; 228/178
(58) Field of Search .............................. 228/175, 178, 228/103, 104; 428/615

(56) References Cited

U.S. PATENT DOCUMENTS

| | | | | |
|---|---|---|---|---|
| 3,610,876 A | * | 10/1971 | Bhat | 219/137 R |
| 4,062,705 A | * | 12/1977 | Gondo et al. | 148/529 |
| 4,817,859 A | * | 4/1989 | Breitenmoser et al. | 228/226 |
| 4,943,702 A | * | 7/1990 | Richardson | 219/124.34 |
| 5,227,609 A | | 7/1993 | Simon et al. | 219/137 R |
| 5,376,766 A | * | 12/1994 | Higgins | 219/61.5 |
| 5,748,318 A | * | 5/1998 | Maris et al. | 356/630 |
| 6,106,710 A | * | 8/2000 | Fischer et al. | 210/198.2 |
| 6,127,643 A | * | 10/2000 | Unde | 219/73 |
| 6,543,670 B2 | * | 4/2003 | Mahoney | 228/112.1 |
| 2003/0201263 A1 | * | 10/2003 | Morikage et al. | 219/136 |
| 2003/0218056 A1 | * | 11/2003 | Fairchild et al. | 228/175 |
| 2004/0031544 A1 | * | 2/2004 | Hara et al. | 148/521 |
| 2004/0069831 A1 | * | 4/2004 | O'Donnell et al. | 228/104 |

FOREIGN PATENT DOCUMENTS

JP              63140798 A    *  6/1988

OTHER PUBLICATIONS

Simon, W. et al., "Repair of Existing Steel Moment Frame Buildings Damaged from Earthquakes Using Fracture Tough Weld Overlays", Engineering Journal, Fourth Quarter 1999, pp. 145–159.

* cited by examiner

Primary Examiner—Kiley S. Stoner

(57) ABSTRACT

Methods for producing toughness-optimized weld joints are provided. A welding procedure that will provide adequate toughness for the center-weld of the weld-joint is developed and used, and a welding procedure that will provide adequate toughness for the surface-weld of the weld-joint is developed and used.

1 Claim, 1 Drawing Sheet

TOUGHNESS-OPTIMIZED WELD JOINTS AND METHODS FOR PRODUCING SAID WELD JOINTS

This application claims the benefit of U.S. Provisional Application No. 60/417,974 that was filed 11 Oct. 2002.

FIELD OF THE INVENTION

The present invention relates generally to the field of welding. More particularly, the invention pertains to weld joints having optimized toughness and to methods for producing said weld joints.

BACKGROUND OF THE INVENTION

Various terms are defined in the following specification. For convenience, a Glossary of terms is provided herein, immediately preceding the claims.

U.S. Pat. No. 6,085,528 (the "PLNG Patent"), having corresponding International Publication Number WO 98/59085 and entitled "System for Processing, Storing, and Transporting Liquefied Natural Gas", describes containers and transportation vessels for storage and marine transportation of pressurized liquefied natural gas ("PLNG") at a pressure in the broad range of about 1035 kPa (150 psia) to about 7590 kPa (1100 psia) and at a temperature in the broad range of about −123° C. (−190° F.) to about −62° C. (−80° F.). Containers described in the PLNG Patent are constructed from ultra-high strength, low alloy steels containing less than 9 wt % nickel ("Steel PLNG Containers"). The PLNG Patent is hereby incorporated herein by reference. As used herein, "ultra-high strength, low alloy steel" means any steel containing iron and less than about 10 wt % total alloy additives and having a tensile strength greater than 830 MPa (120 ksi).

Steel PLNG Containers, as well as other metallic containers for storing pressurized, cryogenic temperature fluids, typically include welded joints. The weld joints must have sufficient resistance to fracture initiation, i.e., toughness, since they may contain discontinuities that can affect the mechanical integrity of a metallic container. See Glossary for definition of weld joint. Typical weld discontinuities include, for example, lack of penetration, lack of fusion, hydrogen cracking, and inclusions. Welding operations can degrade toughness by degrading the metallurgy in what is referred to as the heat-affected-zone ("HAZ"), which is the base metal that is adjacent to the weld fusion line and that was affected by the heat of welding. For certain applications where HAZ toughness is a design limiting issue, common methods of improving and controlling HAZ toughness are to limit welding heat input to low values or to use welding techniques that better control heat input, such as gas tungsten arc welding ("GTAW") instead of submerged arc welding ("SAW"). Unfortunately, these methods are costly in that the welding operations are much more time consuming, expensive equipment and consumables are needed, special training is required for welders, and/or quality control and assurance methods are onerous.

It is desirable to have economically acceptable methods for commercial welding of metallic containers for storing pressurized, cryogenic temperature fluids that provide weld joints with appropriate strength and toughness.

SUMMARY OF THE INVENTION

A method is provided for welding two pieces of metal to produce a weld joint comprised of a center-weld and a surface-weld, and having a specified thickness and optimized toughness for an intended application. Said method comprises the steps of: (a) selecting a first non-destructive examination ("NDE") technique that is suitable for detecting surface-breaking discontinuities in a metal used in said intended application; (b) determining a minimum surface-breaking discontinuity through-thickness dimension that is readily detectable by said first NDE technique; (c) selecting a second NDE technique that is suitable for detecting embedded discontinuities in a metal used in said intended application; (d) determining a minimum embedded discontinuity through-thickness dimension that is readily detectable by said second NDE technique; (e) determining a first toughness value that is adequate to substantially prevent fracture initiation in said weld joint from surface-breaking discontinuities having a through-thickness dimension that is substantially equal to said minimum surface-breaking discontinuity through-thickness dimension and determining a second toughness value that is adequate to substantially prevent fracture initiation in said weld joint from embedded discontinuities having a through-thickness dimension that is substantially equal to said minimum embedded discontinuity through thickness dimension; (f designing a surface-weld welding procedure that will produce a surface-weld having a toughness value substantially equal to or greater than said first toughness value and a center-weld welding procedure that will produce a center-weld having a toughness value substantially equal to or greater than said second toughness value; (g) creating said center-weld using said center-weld welding procedure; and (h) creating said surface-weld using said surface-weld welding procedure. These steps may be performed in any order deemed suitable by one skilled in the art of welding engineering. A weld joint produced by a method according to this invention is also provided.

The inventors note that less toughness is needed to resist fracture initiation from an embedded discontinuity than from a surface-breaking discontinuity of the same size. Therefore, high toughness requirements may be limited to the surface region of the weld joint only, thus minimizing the amount of costly welding operations that are required.

DESCRIPTION OF THE DRAWINGS

The advantages of the present invention may be better understood by referring to the following detailed description and the attached drawings in which.

While the invention is described in connection with its preferred embodiments, it is understood that the invention is not limited thereto. On the contrary, the invention is intended to cover all alternatives, modifications, and equivalents which may be included within the spirit and scope of the present disclosure, as defined by the appended claims.

DETAILED DESCRIPTION OF THE INVENTION

Fracture mechanics theory provides the basis for toughness requirements. According to fracture mechanics theory, for a given material discontinuity size and load, the crack driving force (e.g., without limiting this invention, $J_I$ or $\delta_I$, as is familiar to those skilled in the art of welding engineering) to which an embedded discontinuity is subjected is roughly 2.25 times less than the crack driving force of a similar surface breaking discontinuity. A discontinuity size is typically assumed to be the smallest discontinuity size a specific NDE technique is readily capable of detecting. Since the crack driving force associated with embedded discontinuities is lower than it is for surface breaking discontinuities, the required toughness (e.g., without limiting this invention, $J_c$, $J_u$, $J_{Ic}$, $\delta_c$, $\delta_u$, $\delta_m$, or $\delta_{Ic}$, as is familiar to those skilled in the art of fracture mechanics) to prevent fracture initiation from an embedded discontinuity is roughly 2.25 times less than the required toughness to prevent fracture initiation from a surface-breaking discontinuity. The method of this invention is used to analyze the required toughness to substantially prevent fracture initiation from both surface-breaking and embedded discontinuities and, based on said analysis, to optimize the welding procedure. A higher productivity welding procedure is used to create the center portion of the weld joint (where toughness requirements are not as great) and a welding procedure better able to retain toughness is used to create the surface portion of the weld joint. This invention is not limited to any particular welding procedure. Thus, any welding procedure selected by the welding engineer may be utilized, including without limitation, heat assisted welding, pressure assisted welding, laser welding, or friction stir welding.

Figure 1:
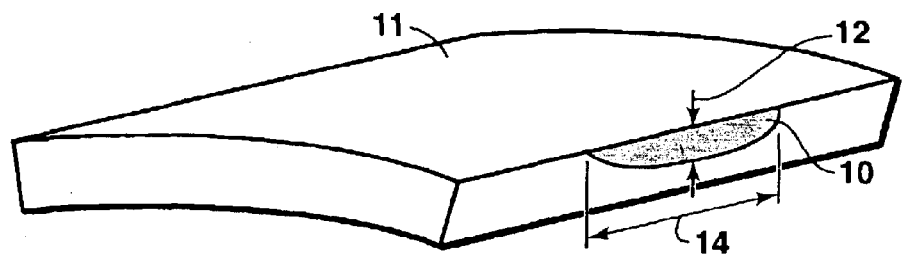
FIG. 1 illustrates a surface-breaking discontinuity.
Figure 2:
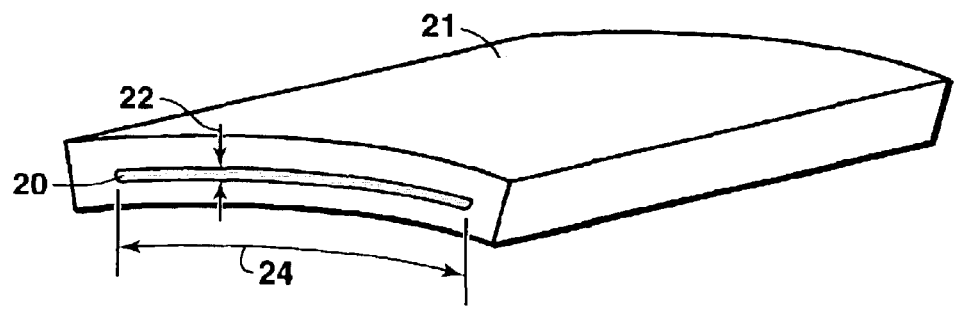
FIG. 2 illustrates an embedded discontinuity.

FIG. 1 illustrates a surface-breaking discontinuity 10 in a piece of metal 11. Said surface-breaking discontinuity 10 has through-thickness dimension 12 and length 14. Said piece of metal 11 may be any piece of metal such as a weld metal, a weld joint, or a base metal. FIG. 2 illustrates an embedded discontinuity 20 in a piece of metal 21. Said embedded discontinuity 20 has through-thickness dimension 22 and length 24. Said piece of metal 21 may be any piece of metal such as a weld metal, a weld joint, or a base metal.

A method of welding two pieces of metal to produce a weld joint comprised of a center-weld and a surface-weld, and having a specified thickness and optimized toughness for an intended application according to this invention comprises the following steps. A first non-destructive examination ("NDE") technique suitable for detecting surface-breaking discontinuities in a metal used for said intended application is selected. One skilled in the art of welding engineering is capable of selecting an appropriate NDE technique, for example, without limiting this invention, radiography or an ultrasonic technique such as pulse echo, or time of flight diffraction. Based on the selected first NDE technique, a minimum surface-breaking discontinuity through-thickness dimension that is readily detectable by said first NDE technique is determined. For example, if ultrasonic examination ("UT") is specified, the minimum through-thickness dimension for a surface-breaking discontinuity would be the smallest surface-breaking discontinuity that is readily detectable by the specific UT procedure and equipment employed. As used herein, the term "NDE technique" includes both the NDE procedure and NDE equipment. As used herein, the term "readily detectable" in regard to discontinuity through-thickness dimension means the through-thickness dimension of a discontinuity that can be detected and repaired regardless of its position or orientation. A second non-destructive examination ("NDE") technique suitable for detecting embedded discontinuities in a metal used for said intended application is selected. Based on the selected second NDE technique, a minimum embedded discontinuity through-thickness dimension that is readily detectable by said second NDE technique is determined. Preferably the minimum surface-breaking discontinuity through-thickness dimension is less than about 33% of said specified thickness of said weld joint. A first target toughness value that is adequate to prevent fracture initiation in said weld joint from surface-breaking discontinuities having a through-thickness dimension that is substantially equal to said minimum surface-breaking discontinuity through-thickness dimension is determined, and a second toughness value that is adequate to prevent fracture initiation in said weld joint from embedded discontinuities having a through-thickness dimension that is substantially equal to said minimum embedded discontinuity through thickness dimension is determined. Said first and second target toughness values are determined by any means known to those skilled in the art of fracture mechanics, e.g., by an analysis based on fracture mechanics procedures, such as BS7910 (Guide on Methods for Assessing the Acceptability of Flaws in Metallic Structures) or API RP579 (Fitness for Service). A surface-weld welding procedure is designed that will produce a surface-weld having a toughness value that is substantially equal to or greater than said first toughness value, i.e., that will provide adequate toughness to substantially prevent fracture initiation from surface-breaking discontinuities having a through-thickness dimension that is substantially equal to said minimum surface-breaking discontinuity through-thickness dimension, and a center-weld welding procedure is designed that will produce a center-weld having a toughness value that is substantially equal to or greater than said second toughness value, i.e., that will provide adequate toughness to substantially prevent fracture initiation from embedded discontinuities having a through-thickness dimension that is substantially equal to said minimum embedded discontinuity through-thickness dimension. Welding procedures may be designed to provide needed toughness values by those skilled in the art of welding engineering using well known techniques. The center-weld is created using the center-weld welding procedure, and the surface-weld is created using the surface-weld welding procedure. As used herein, "through-thickness dimension of a surface-breaking discontinuity" means the dimension 12 of a surface-breaking discontinuity through the thickness of said pieces of metal or of said weld joint, as shown in FIG. 1. As used herein, "through-thickness dimension of an embedded discontinuity" means the dimension 22 of an embedded discontinuity through the thickness of said pieces of metal or of said weld joint, as shown in FIG. 2. The required thickness, or minimum required thickness, of the surface-weld should also be determined by means familiar to those skilled in the art of welding engineering and fracture mechanics. The minimum required thickness of said surface-weld is typically slightly greater (e.g., about 1 mm greater) than the minimum surface-breaking discontinuity through-thickness dimension. The surface-weld preferably has a thickness that is equal to or greater than the required surface-weld thickness.

The surface-weld welding procedure and the center-weld welding procedure may be qualified by any means known to those skilled in the art of welding engineering, for example the procedures for measuring the toughness of welds described in BS7910. As used herein, the term "to qualify" means to measure properties, including toughness, of a weld joint to be above the minimum necessary according to a standard procedure. As is familiar to those skilled in the art of welding engineering, a toughness value that is adequate to substantially prevent fracture initiation in a metal from a discontinuity having a specified through-thickness dimension is also capable of preventing fracture initiation in the metal from a discontinuity having a through-thickness dimension that is smaller or less than said specified through-thickness dimension. As will also be familiar to those skilled in the art of welding engineering, any surface-breaking discontinuities in said weld joint having a through-thickness dimension that is greater than the minimum surface-breaking discontinuity through-thickness dimension are repaired; and any embedded discontinuities in said weld joint having a through-thickness dimension that is greater than the minimum embedded discontinuity through-thickness dimension are repaired.

Figure 3:
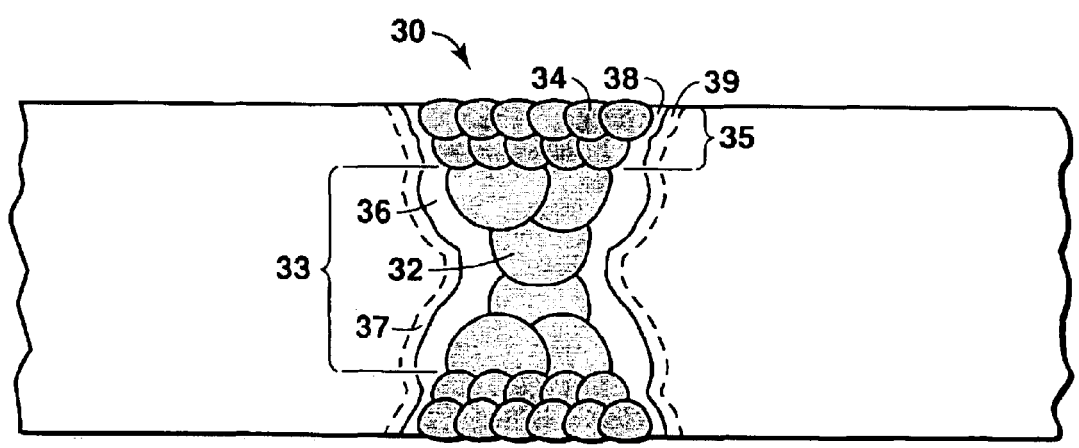
FIG. 3 illustrates a toughness-optimized weld joint produced according to this invention.

FIG. 3 illustrates a toughness-optimized weld joint 30 produced with a center-weld 33 and a surface-weld 35 according to this invention. In this non-limiting example, heat-assisted welding procedures are used and, thus, heat-affected-zones are formed. The thickness of the center-weld 33 and the number of weld passes required to produce center-weld 33 are determined by methods known to those skilled in the art of welding engineering considering the minimum required thickness of the surface-weld 35 and the specified thickness of the weld joint 30. The minimum required thickness of the surface-weld 35 and the number of weld passes required to produce surface-weld 35 are determined by methods known to those skilled in the art of welding engineering considering the minimum surface-breaking discontinuity through-thickness dimension. Center-weld 33 includes center-weld metal 32, center-weld HAZ 36, and center-weld affected base metal 37, all as produced and affected by the center-weld welding procedure. Surface-weld 35 includes surface-weld metal 34, surface-weld HAZ 38, and surface-weld affected base metal 39, all as produced and affected by the surface-weld welding procedure. The welding procedures used to produce surface-weld 35 and center-weld 33 are different. For example, surface-weld HAZ 38 created by the surface-weld welding procedure has a higher required toughness value than center-weld HAZ 36 created by the center-weld welding procedure. The center-weld welding procedure requires fewer weld passes for a given amount of wall thickness covered, and thus it is faster and less expensive to use than the surface-weld welding procedure.

Qualifying toughness-optimized weld joints made according to this invention is preferably accomplished by measuring the discontinuity-specific toughness, which as described in BS7910 (Guide on Methods for Assessing the Acceptability of Flaws in Metallic Structures), Annex L (Fracture Toughness Determination for Welds), Section 4.3 (Specimen Geometry) measures the toughness associated with appropriate discontinuities. Two specific methods of accomplishing this for toughness-optimized weld joints are described as follows, both of which are familiar to those skilled in the art of fracture mechanics: (i) Measure the toughness using BS7448-2 (with either through-thickness or surface notched specimen) of two sets of specimens. The first set of specimens is manufactured using only the weld procedure for the center portion of the weld joint, and the thickness of the entire joint is completed using this procedure. The second set of specimens is manufactured using only the surface-weld welding procedure, and the thickness of the entire joint is completed using this procedure; or (ii) Measure the toughness in two locations of a toughness-optimized weld made in accordance with this invention. The toughness of the surface weld can be measured using shallow surface notches. The toughness of the center weld can be measured using surface notches having the standard depth, as is familiar to those skilled in the art of fracture mechanics.

EXAMPLE

Ultra-high strength, low alloy steel plates for constructing Steel PLNG Containers suitable for transport of PLNG requires weld qualification based on fracture toughness (such as J-integral or CTOD) testing, and a minimum required (target) toughness value must be achieved. Fracture-mechanics-based analyses are performed to derive the target J-integral value for weld joints in a PLNG Container. The analyses assume that a single weld discontinuity, having a maximum through-thickness dimension of 2 mm and a length of 100 mm, exists in any possible location and orientation in the PLNG Container, based on the capabilities of currently available NDE techniques. The limiting weld discontinuity type, a surface-breaking weld discontinuity, is chosen as the controlling discontinuity type, and the resulting target J-integral value is derived.

A weld procedure is developed to reliably produce a weld joint satisfying the required J-integral value without the use of this invention. The procedure is a GTAW technique with low heat input (about 1 kJ/mm) and low travel speed (about 250 mm/min). This GTAW welding technique requires an autogenous pass after each primary pass to temper the HAZ microstructure. The result is a welding procedure requiring approximately 50 passes and an effective welding speed of 5 mm/min. Since there are approximately 300 meters of ultra-high strength, low alloy steel weld length for each PLNG container, 85 welding machines, operating 24 hours a day, 7 days a week, at 100% efficiency, will be needed to produce 2 PLNG containers each day. It is anticipated that reducing the number of welding stations by as much as 75% will reduce container fabrication costs considering both CAPEX (e.g., number of welding machines) and OPEX (e.g., salary of welding operators) significantly enough to affect overall project economics.

The fracture-mechanics-based analysis is revisited specifically considering embedded discontinuities. According to fracture mechanics theory, comparing a surface-breaking discontinuity with an embedded discontinuity each having the same through-thickness dimension, the target toughness to substantially prevent fracture initiation from the surface-breaking discontinuity is more than double the target toughness to substantially prevent fracture from an embedded discontinuity. Therefore, a different welding procedure, one producing less toughness, may be used for producing the mid-wall-thickness section of the weld joint (approximately the center 1.84 cm of a 2.54 cm-thick weld joint) in accordance with this invention.

The original welding procedure, i.e., the GTAW method with low heat input (about 1 kJ/mm) and low travel speed (about 250 mm/min) that requires an autogenous pass after each primary pass to temper the HAZ microstructure, will provide sufficient toughness to substantially prevent fracture initiation from surface-breaking discontinuities. Therefore, the original welding procedure is designated for producing the surface-weld. Since the principle drawback of the original welding procedure is its low productivity rate, a procedure with higher productivity rate is desired for the center 1.84 cm of the weld. An incremental increase in heat input and weld metal deposition rate using either GTAW or gas metal arc welding ("GMAW") welding processes will provide initial benefit. Because of their high production rate, laser and electron beam welding procedures can be considered. Weldments are produced and tested to determine the appropriate center weld procedure. Weldments are produced using the selected center weld procedure and surface weld procedure.

Although this invention is well suited for welding of steel containers for storing pressurized, cryogenic temperature fluids, in particular PLNG Containers, it is not limited thereto; rather, this invention is suitable for welding of any steel structures. Weld joints produced according to this invention may be applied to applications other than ultra-high strength, low alloy steels, provided a fracture-mechanics-based analysis has been conducted and the critical surface-breaking discontinuity size is small relative to the wall thickness. Applications other than PLNG that may benefit from toughness-optimized weld joints according to this invention include, for example without limiting this invention, pressure vessels, piping and pipeline, and steel structures.

Additionally, while the present invention has been described in terms of one or more preferred embodiments, it is to be understood that other modifications may be made without departing from the scope of the invention, which is set forth in the claims below.

GLOSSARY OF TERMS cryogenic temperature: any temperature of about −40° C. (−40° F.) or colder;

discontinuity: an interruption of the typical structure of a weldment, such as a lack of homogeneity in the mechanical, metallurgical, or physical characteristics of the weldment;

GMAW: gas metal arc welding;

GTAW: gas tungsten arc welding;

HAZ: heat-affected-zone;

heat-affected-zone: base metal that is adjacent to the weld fusion line and that was affected by the heat of welding;

$J_I$, $\delta_I$: symbols designating crack driving force measurements, as is familiar to those skilled in the art of welding engineering;

$J_c$, $J_u$, $J_{Ic}$, $\delta_c$, $\delta_u$, $\delta_m$, $\delta_{Ic}$: symbols designating toughness measurements, as is familiar to those skilled in the art of welding engineering;

NDE: non-destructive examination;

NDE technique: includes both the NDE procedure and NDE equipment;

qualify: to measure properties, including toughness, of a weld joint to be above the minimum necessary according to a standard procedure;

readily detectable: in regard to discontinuity through-thickness dimension, means the through-thickness dimension of a discontinuity that can be detected and repaired regardless of its position or orientation;

SAW: submerged arc welding;

through-thickness dimension of a surface-breaking discontinuity: the dimension (i.e., length) of the surface-breaking discontinuity through the thickness of the piece of metal or weld joint in which the surface-breaking discontinuity exists;

through-thickness dimension of an embedded discontinuity: the dimension (i.e., length) of the embedded discontinuity through the thickness of the piece of metal or weld joint in which the embedded discontinuity exists;

toughness: resistance to fracture initiation;

ultra-high strength, low alloy steel: any steel containing iron and less than about 10 wt % total alloy additives and having a tensile strength greater than 830 MPa (120 ksi);

weld joint: A welded joint, including the fused metal and the base metal in the "near vicinity" of, but beyond, the fused metal. The weld joint may or may not contain either added weld metal or a heat-affected-zone ("HAZ"). The portion of the base metal that is considered within the "near vicinity" of the fused metal, and therefore, a part of the weld joint, varies depending on factors known to those skilled in the art of welding engineering, for example, without limitation, the width of the weld joint, the size of the item that was welded, the number of weld joints required to fabricate the item, and the distance between weld joints. Possible techniques to create a weld joint include, but are not limited to, heat assisted welding, pressure assisted welding, laser welding, and friction stir welding.

weldment: an assembly whose component parts are joined by welding.

We claim:

1. A method of welding two pieces of metal to produce a weld joint comprised of a center-weld and a surface-weld, and having a specified thickness and optimized fracture toughness for an intended application, said method comprising the stops of:

(a) selecting a first non-destructive examination technique that is suitable for detecting surface-breaking discontinuities in a metal used in said intended application;

(b) determining a minimum surface-breaking discontinuity through-thickness dimension that is readily detectable by said first non-destructive examination technique;

(c) selecting a second non-destructive examination technique that is suitable for detecting embedded discontinuities in a metal used in said intended application;

(d) determining a minimum embedded discontinuity through-thickness dimension that is readily detectable by said second non-destructive examination technique;

(e) determining a first toughness value that is adequate to substantially prevent fracture initiation in said weld joint from surface-breaking discontinuities having a through-thickness dimension that is substantially equal to said minimum surface-breaking discontinuity through-thickness dimension and a second toughness value that is adequate to substantially prevent fracture initiation in said weld joint from embedded discontinuities having a through-thickness dimension that is substantially equal to said minimum embedded discontinuity through thickness dimension;

(f) designing a surface-weld welding procedure that will produce a surface-weld having a toughness value substantially equal to or greater than said first toughness value and a center-weld welding procedure that will produce a center-weld having a toughness value substantially equal to or greater than said second toughness value;

(g) creating said center-weld using said center-weld welding procedure; and (h) creating said surface-weld using said surface-weld welding procedure.

* * * * *